United States Patent
Jaaskelainen et al.

(10) Patent No.: US 11,054,536 B2
(45) Date of Patent: Jul. 6, 2021

(54) TRANSLATABLE EAT SENSING MODULES AND ASSOCIATED MEASUREMENT METHODS

(71) Applicant: Halliburton Energy Services, Inc., Houston, TX (US)

(72) Inventors: Mikko Jaaskelainen, Katy, TX (US); Seldon David Benjamin, Spring, TX (US); Brian V. Park, Spring, TX (US); Jason Edward Therrien, Cypress, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 224 days.

(21) Appl. No.: 16/338,945

(22) PCT Filed: Dec. 1, 2016

(86) PCT No.: PCT/US2016/064338
§ 371 (c)(1),
(2) Date: Apr. 2, 2019

(87) PCT Pub. No.: WO2018/101942
PCT Pub. Date: Jun. 7, 2018

(65) Prior Publication Data
US 2021/0033739 A1 Feb. 4, 2021

(51) Int. Cl.
*G01V 1/22* (2006.01)
*E21B 49/08* (2006.01)
(Continued)

(52) U.S. Cl.
CPC ............ *G01V 1/226* (2013.01); *E21B 23/001* (2020.05); *E21B 47/06* (2013.01); *E21B 47/07* (2020.05);
(Continued)

(58) Field of Classification Search
CPC .............................. G01V 1/226; E21B 23/001
See application file for complete search history.

(56) References Cited

U.S. PATENT DOCUMENTS 5,947,213 A * 9/1999 Angle .................... E21B 47/002
   175/24
6,026,911 A * 2/2000 Angle ..................... E21B 17/10
   175/24
(Continued)

FOREIGN PATENT DOCUMENTS

| EP | 1830035 A1 | 9/2007 |
| WO | 2016144337 A1 | 9/2016 |
| WO | 2017105435 A1 | 6/2017 |

OTHER PUBLICATIONS

PCT Application Serial No. PCT/US2016/064338, International Search Report, dated Aug. 30, 2017, 5 pages.
(Continued)

*Primary Examiner* — John Fitzgerald
(74) *Attorney, Agent, or Firm* — Gilliam IP PLLC

(57) ABSTRACT

A system of translatable electro acoustic technology (EAT) modules for deployment along an oil or gas wellbore casing includes: a wireline/slickline optical distributed acoustic sensing (DAS) cable deployed from the surface into the casing and connected to a surface interrogator; a tractor attached to the downhole end of the wireline/slickline optical distributed acoustic sensing (DAS) cable; and one or more EAT sensing modules that can be coupled to or decoupled from the wireline/slickline optical distributed acoustic sensing (DAS) cable at pre-selected locations and can either be coupled to or decoupled from the casing of the wellbore or be allowed to reposition along the wellborn casing, wherein the one or more EAT sensing modules can conduct multiple measurements and communicate the
(Continued)

results via the wireline/slickline optical distributed acoustic sensing (DAS) cable to the surface interrogator.

20 Claims, 10 Drawing Sheets

(51) Int. Cl.
    *E21B 47/07*         (2012.01)
    *E21B 23/00*        (2006.01)
    *E21B 47/135*      (2012.01)
    *E21B 47/06*        (2012.01)
    *E21B 47/14*        (2006.01)
    *G01N 9/00*         (2006.01)
    *G01N 33/28*       (2006.01)

(52) U.S. Cl.
    CPC ............ *E21B 47/135* (2020.05); *E21B 47/14* (2013.01); *E21B 49/0875* (2020.05); *G01N 9/00* (2013.01); *G01N 33/2847* (2013.01)

(56) References Cited

U.S. PATENT DOCUMENTS

| | | | | |
|---|---|---|---|---|
| 6,112,809 A * | 9/2000 | Angle | ................ | E21B 17/1021 166/66 |
| 6,241,028 B1 | 6/2001 | Bijleveld et al. | | |
| 6,431,270 B1 * | 8/2002 | Angle | ................ | E21B 47/26 166/66.5 |
| 7,048,089 B2 | 5/2006 | West | ................ | G01V 1/16 181/105 |
| 7,178,627 B2 * | 2/2007 | West | ................ | G01V 1/16 181/105 |
| 10,267,140 B2 * | 4/2019 | Andreychuk | ......... | E21B 47/002 |
| 10,267,144 B2 * | 4/2019 | Hazel | ................ | E21B 47/01 |
| 10,465,482 B2 * | 11/2019 | Jaaskelainen | ............ | H02J 7/00 |
| 10,711,599 B2 * | 7/2020 | Jaaskelainen | ........... | E21B 23/10 |
| 2004/0223410 A1 * | 11/2004 | West | ................ | G01V 1/40 367/25 |
| 2006/0175125 A1 * | 8/2006 | West | ................ | G01V 1/40 181/122 |
| 2007/0193776 A1 | 8/2007 | Luling | | |
| 2009/0271117 A1 * | 10/2009 | Ayoub | ................ | G01V 11/002 702/11 |
| 2012/0057432 A1 | 3/2012 | Hill et al. | | |
| 2014/0102794 A1 * | 4/2014 | Tevis | ................ | E21B 25/16 175/44 |
| 2014/0116726 A1 * | 5/2014 | Airey | ................ | E21B 23/01 166/381 |
| 2014/0150523 A1 | 6/2014 | Stokely et al. | | |
| 2016/0003648 A1 * | 1/2016 | Barfoot | ................ | E21B 47/135 250/227.19 |
| 2016/0186554 A1 * | 6/2016 | Burgos | ................ | E21B 47/113 166/250.01 |
| 2016/0215578 A1 * | 7/2016 | Adnan | ................ | E21B 23/14 |
| 2016/0230505 A1 * | 8/2016 | Garcia | ................ | E21B 47/12 |
| 2016/0282488 A1 | 9/2016 | Sallas et al. | | |
| 2016/0356145 A1 * | 12/2016 | Andreychuk | ......... | E21B 47/002 |
| 2017/0096892 A1 * | 4/2017 | Segura Dominguez | | E21B 17/206 |
| 2017/0114628 A1 * | 4/2017 | Khalaj Amineh | .... | E21B 47/085 |
| 2017/0138177 A1 * | 5/2017 | Hazel | ................ | E21B 47/06 |
| 2017/0314341 A1 * | 11/2017 | Lovell | ................ | E21B 47/135 |
| 2017/0314372 A1 * | 11/2017 | Tolman | ................ | E21B 43/116 |
| 2017/0350237 A1 * | 12/2017 | Giem | ................ | E21B 23/14 |
| 2018/0283143 A1 * | 10/2018 | Jaaskelainen | ............ | H02J 7/00 |
| 2019/0203576 A1 * | 7/2019 | Andreychuk | ............ | G01V 1/46 |

OTHER PUBLICATIONS

PCT Application Serial No. PCT/US2016/064338, International Written Opinion, dated Aug. 30, 2017, 5 pages.

CA Application Serial No. 3036228, First Office Action dated Mar. 12, 2020, 4 pages.

Kragas, et al., "Downhole Fiber-Optic Multiphase Flowmeter: Design, Operating Principle, and Testing", Society of Petroleum Engineers Inc, SPE Annual Technical Conference & Exhibition, Texas, 2002, 7 pages.

\* cited by examiner

TRANSLATABLE EAT SENSING MODULES AND ASSOCIATED MEASUREMENT METHODS

BACKGROUND

Real-time downhole multiphase flow rate data is widely understood to be of significant value for production optimization. Despite the potential value of gathering this type of data, reliable continuous measurements of things like downhole flow rates in producing wells have not been available because of difficulties in designing and deploying measurement devices along extended wellbore casings. The ability to gather that data in an efficient manner can be very challenging.

In typical logging deployments the tools are attached to the end of a cable, or in some instances at relatively regular intervals along a cable. These are typically fixed connections as electrical conductors or optical fibers from the cable must be hardwired to the tool. There is no ability to reconfigure the tool string while downhole. Heavy arrays of tools may also be difficult to pull through the horizontal section of a well.

There is a need then for new approaches. Proposed herein is such an approach, making use of a new technology recently developed called electro acoustic technology (EAT) coupled with a new approach to make the EAT modules translatable through the casing of the wellbore. The tool string can be reconfigured.

DETAILED DESCRIPTION

Figure 1:
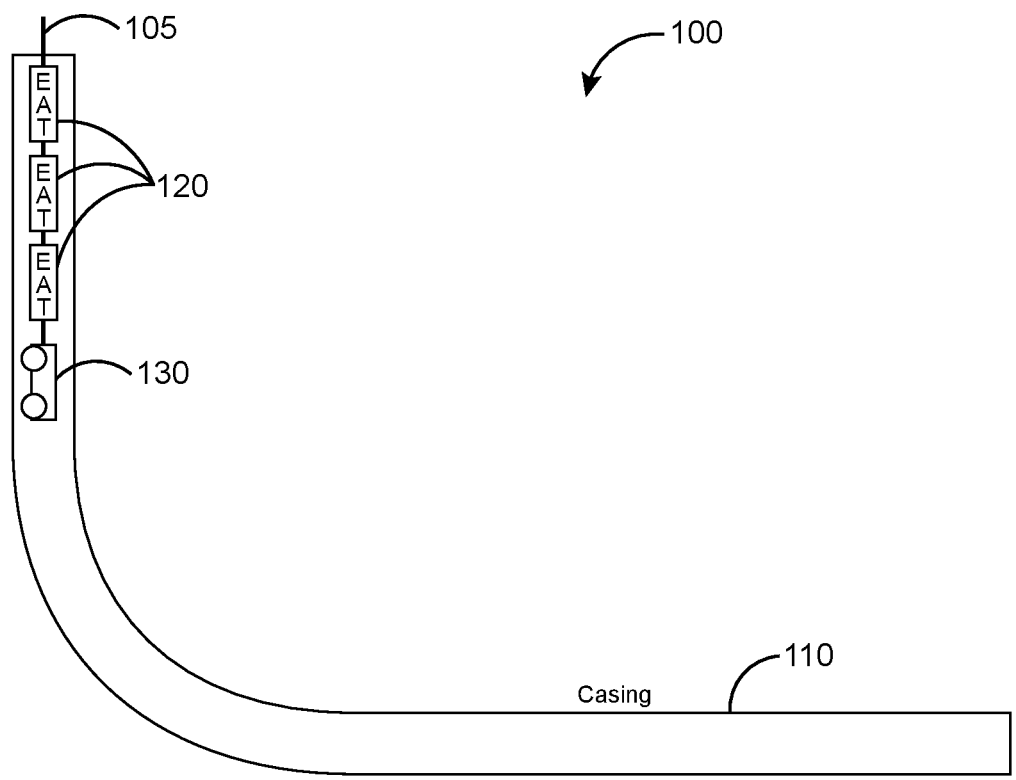
FIG. 1 illustrates a series of Electro Acoustic Technology (EAT) sensor assemblies coupled to a cable and being moved downhole with a tractor.

In the following detailed description, reference is made to accompanying drawings that illustrate embodiments of the present disclosure. These embodiments are described in sufficient detail to enable a person of ordinary skill in the art to practice the disclosure without undue experimentation. It should be understood, however, that the embodiments and examples described herein are given by way of illustration only, and not by way of limitation. Various substitutions, modifications, additions, and rearrangements may be made without departing from the spirit of the present disclosure. Therefore, the description that follows is not to be taken in a limited sense, and the scope of the present disclosure will be defined only by the final claims.

Here we disclose a system and method of using EAT sensing modules that are translatable in that they can be selectively coupled or decoupled to a cable and either coupled to the casing, or be allowed to reposition along the wellbore casing. This represents a flexible deployment system that enables new measurement capability. This takes advantage of a key capability of EAT in that it does not need to be hardwired to a cable (only in close proximity) as data from EAT is communicated acoustically to a DAS fiber in the cable.

Description of EAT (Electro Acoustic Technology) Sensors

The EAT sensors and EAT sensing technology described in this disclosure is a recently developed technology and has been described in a recently published PCT application: WO2015020642A1.

EAT Sensors represent a new approach to fiber optic sensing in which any number of sensors, electronic or fiber optic based, are located in the EAT sensor can be utilized to make the basic parameter measurements, but all of the resulting information is converted at the measurement location into perturbations or a strain applied to an optical fiber that is connected to a surface interrogator. Importantly the wireline/slickline optical distributed acoustic sensing (DAS) cable needs to be in close proximity but does not have to be in direct contact with the source of the perturbations. The surface interrogator may routinely fire optical signal pulses into the optical fiber. As the pulses travel down the optical fiber back scattered light is generated and is received by the interrogator.

Thus, any electro acoustic technology (EAT) module will include at least one sensor, will have internal electronics and a battery, and will include a device that transmit acoustic signals that can be received by the wireline/slickline optical distributed acoustic sensing (DAS) cable, and converted from the measured signals to a physical quality by the interrogator and/or a computer tied to the interrogator. The interrogator may be operate using interferometric sensing principles that may include coherent Rayleigh back scattering, Fabry-Perot interferometers based on FBG's periodically spaced on the optical fiber in the wireline or slick line cable or other similarly suited optical sensing technologies known to a person skilled in the art.

The perturbations or strains introduced to the optical fiber at the location of the various EAT sensors can alter the back propagation of light and those effected light propagations can then provide data with respect to the signal that generated the perturbations.

The possible advantages from using the above described EAT systems in a variety of configurations may include using a variety of sensors, either electrical or fiber optic based, to measure for example a chemical concentration, a pH, a temperature, or a pressure and using a common optical fiber connected to a interrogator to measure perturbation signals from each EAT sensor assembly location distributed along that common optical fiber and analyzing those signals to extract values of the parameters being measured. Regardless of the types of sensors used all of the information to the surface is sent by DAS telemetry. The approach can significantly reduce manufacturing complexity, reduce very expensive labor intensive production with expensive equipment like splicers and fiber winders, improve reliability, and widen industry acceptance by allowing the use of sensing technologies of choice.

The advantage of EAT sensors are further expanded in this disclosure by proposing a system and method that makes the EAT sensing module translatable completely along a wellbore casing.

The Proposal

Disclosed herein is a flexible deployment system utilizing EAT modules as sensing devices in a downhole environment in oil and/or downhole casings and deploying them in a translatable manner that allows them to be moved to desired locations, securely mounted, and later moved or removed as needed. The use of EAT technology makes the proposed system viable because EAT sensors do not need to be hardwired to cable since the data from EAT modules is communicated acoustically to a DAS fiber located in a downhole cable.

The proposal is for a system of translatable electro acoustic technology (EAT) modules for deployment along an oil or gas wellbore casing including at least: a wireline/slickline optical distributed acoustic sensing (DAS) cable deployed from the surface into the casing and connected to a surface interrogator; a tractor attached to the downhole end of the wireline/slickline optical distributed acoustic sensing (DAS) cable; one or more EAT sensing modules that can be coupled to or decoupled from the wireline/slickline optical distributed acoustic sensing (DAS) cable at pre-selected locations and can either be coupled to or decoupled from the casing of the wellbore or be allowed to reposition along the wellbore casing; wherein the one or more EAT sensing modules can conduct multiple measurements and communicate the results via the wireline/slickline optical distributed acoustic sensing (DAS) cable to the surface interrogator system.

The system can be understood in relation to the accompanying figures. Referring first to FIG. 1, shown generally as 100, a down hole casing 110 is illustrated with a wireline or slickline cable 105 with a tractor 130 and three electro acoustic technology (EAT) sensor modules 120. The use of only three EAT's is for illustration purposes only as more could be included. The modules could be attached to the tractor as a unit and as the tractor moves down the casing the individual mechanisms (to be shown) can release the modules and fix them in place at chosen places along the casing. Mechanisms for doing that will be shown in later figures.

It is important to note that although it is not shown in this and following drawings, each of the blocks shown as EAT modules will include at least one sensor, will have internal electronics and a battery, and will include a device that transmit acoustic signals that can be received by the wireline/slickline optical distributed acoustic sensing (DAS) cable, and converted from the measured signals to a physical quality by the interrogator and/or a computer tied to the interrogator. The interrogator may be operate using interferometric sensing principles that may include coherent Rayleigh back scattering, Fabry-Perot interferometers based on FBG's periodically spaced on the optical fiber in the wireline or slick line cable or other similarly suited optical sensing technologies known to a person skilled in the art.

Figure 2:
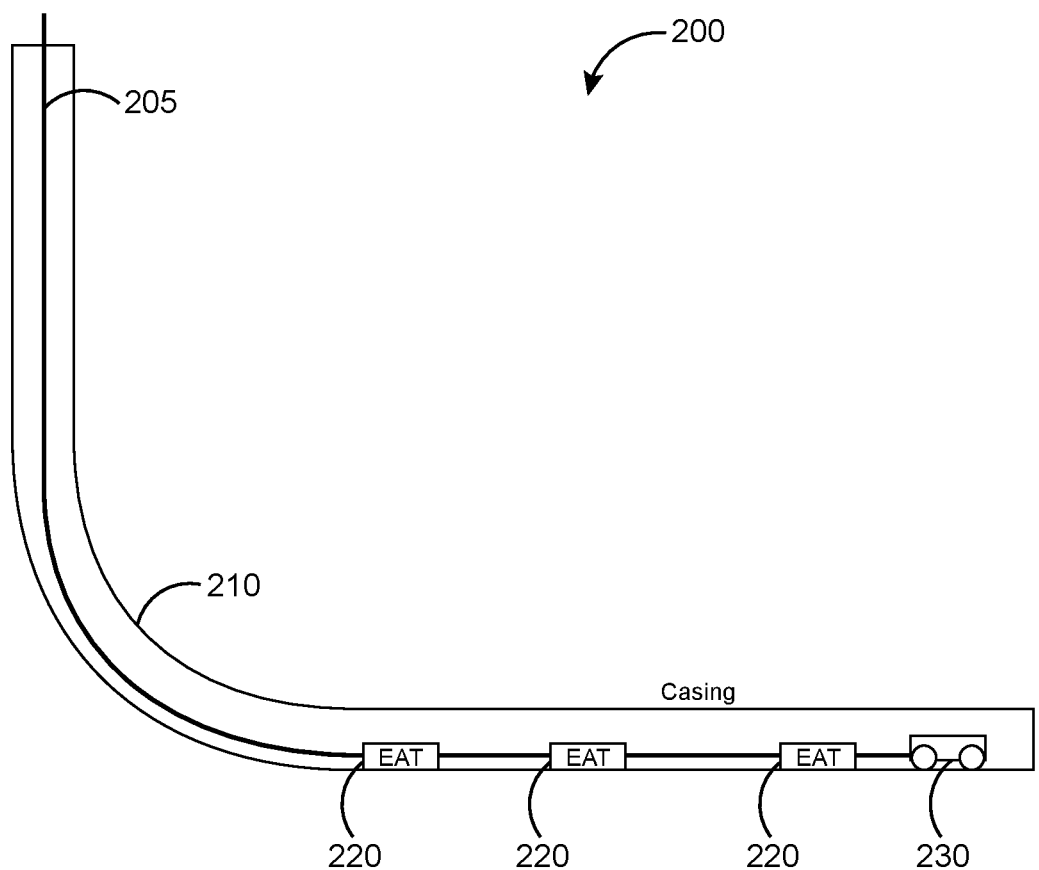
FIG. 2 illustrates EAT's decoupled from cable, one by one, at desired locations downhole.

FIG. 2, shown generally as 200, illustrates a possible later time period when further downhole in the casing 210 the three EAT's 220 that were pulled down the casing by tractor 230 are decoupled from the cable 205, one by one, at desired locations downhole.

Figure 3:
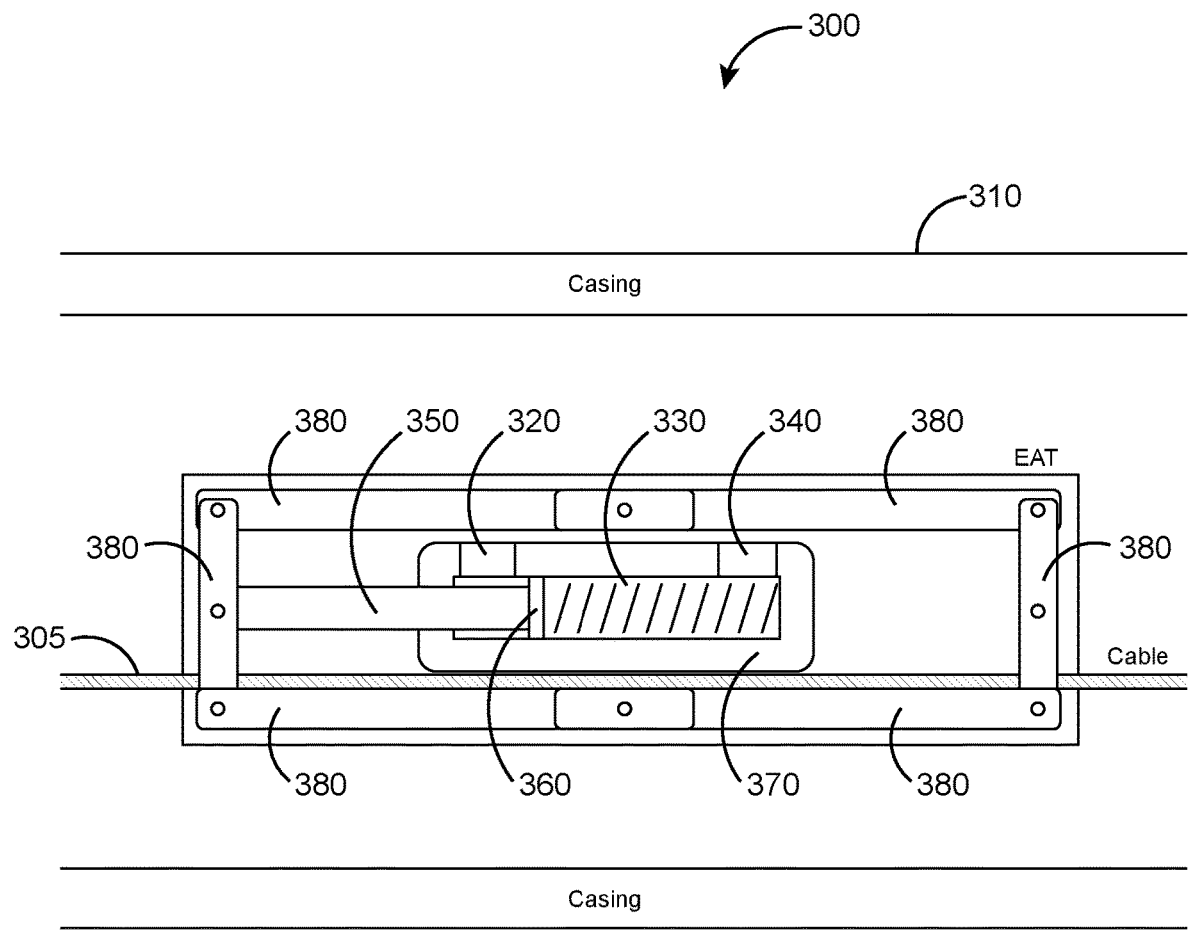
FIG. 3 illustrates an EAT secured to a cable for positioning in wellbore casing. The cable is coupled to the EAT.

To illustrate how the EAT's can be coupled and decoupled from the cable during operations we turn to the remaining figures. In FIG. 3, shown generally as 300, an EAT module is illustrated rigidly clamped to a cable 305 within casing 310. Within the interior of the EAT module is a plunger clamping mechanism 370 to be used to initiate coupling of the EAT module to the casing. A rod 350 on the interior of the plunger clamping mechanism has an expanded spring 330 attached at a sealed end 360 of the rod. Rod 350 is also connected to coupling arms 380 that are deployed to couple the EAT module to the casing. That coupling will be shown in FIG. 4. Two burst disks, a low pressure burst disk 320 and a high pressure burst disk 340 are located on either side of the sealed end 360 of the rod 350. In this configuration the EAT module remains securely coupled to cable 305.

Figure 4:
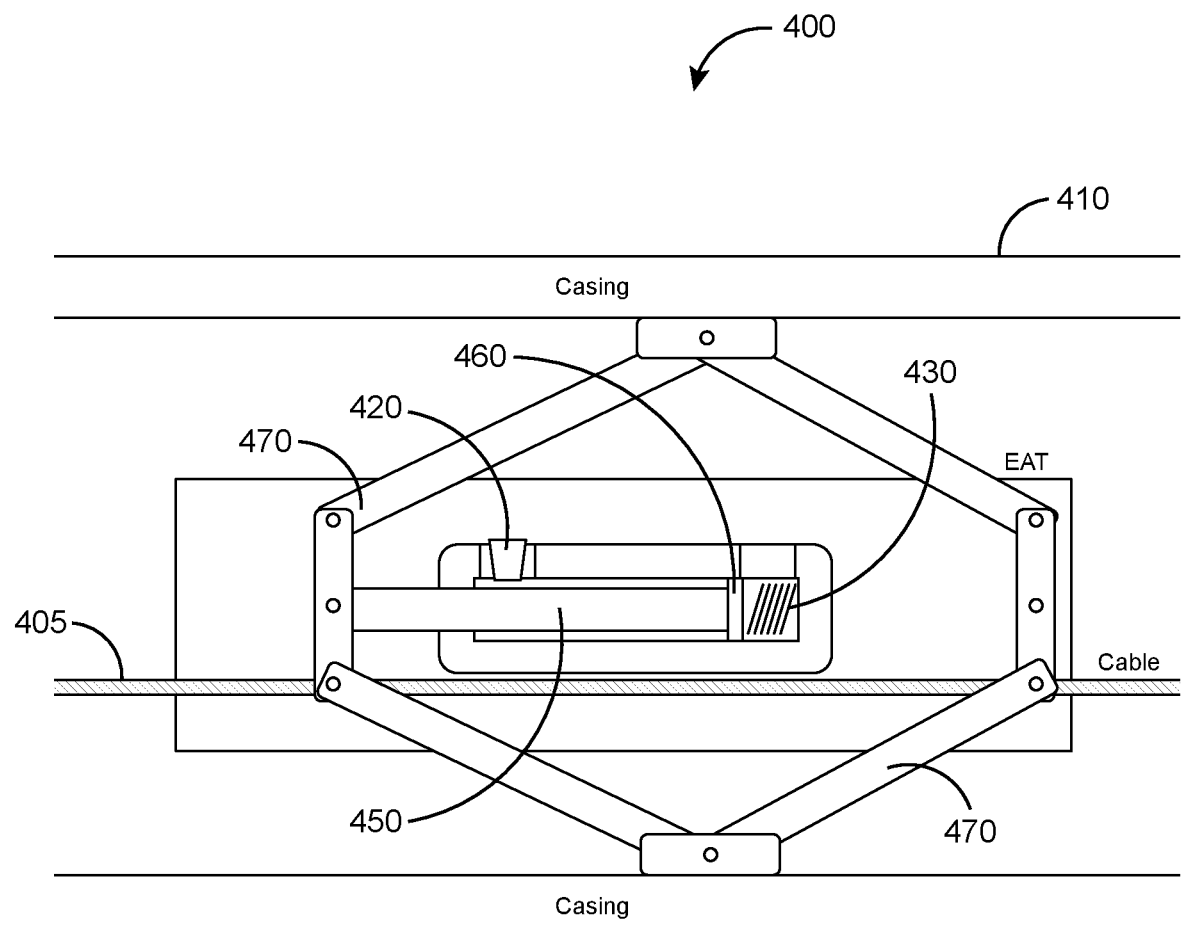
FIG. 4 illustrates an EAT locked in the wellbore casing with the cable uncoupled from the EAT.

When the EAT module is at a desired location for placement in the casing the pressure in the wellbore casing is raised (from the surface) to a pressure that initiates a burst of the low pressure burst disk 320. The result is illustrated in FIG. 4, shown generally as 400. Burst disk 420 has burst and higher pressure enters the interior to the left of the sealed end 460 of the rod 450 and compresses the spring 430 to the right in the figure, pulling the left member of the coupling arms 470 inward, expanding the arms outward to simultaneously lock the EAT module into place against the wellbore casing 410 and uncoupling the EAT module from the cable 405. Cable 405 can continue to move through the wellbore casing but remains in close proximity to the EAT module to receive any acoustic signals from the EAT module.

Figure 5:
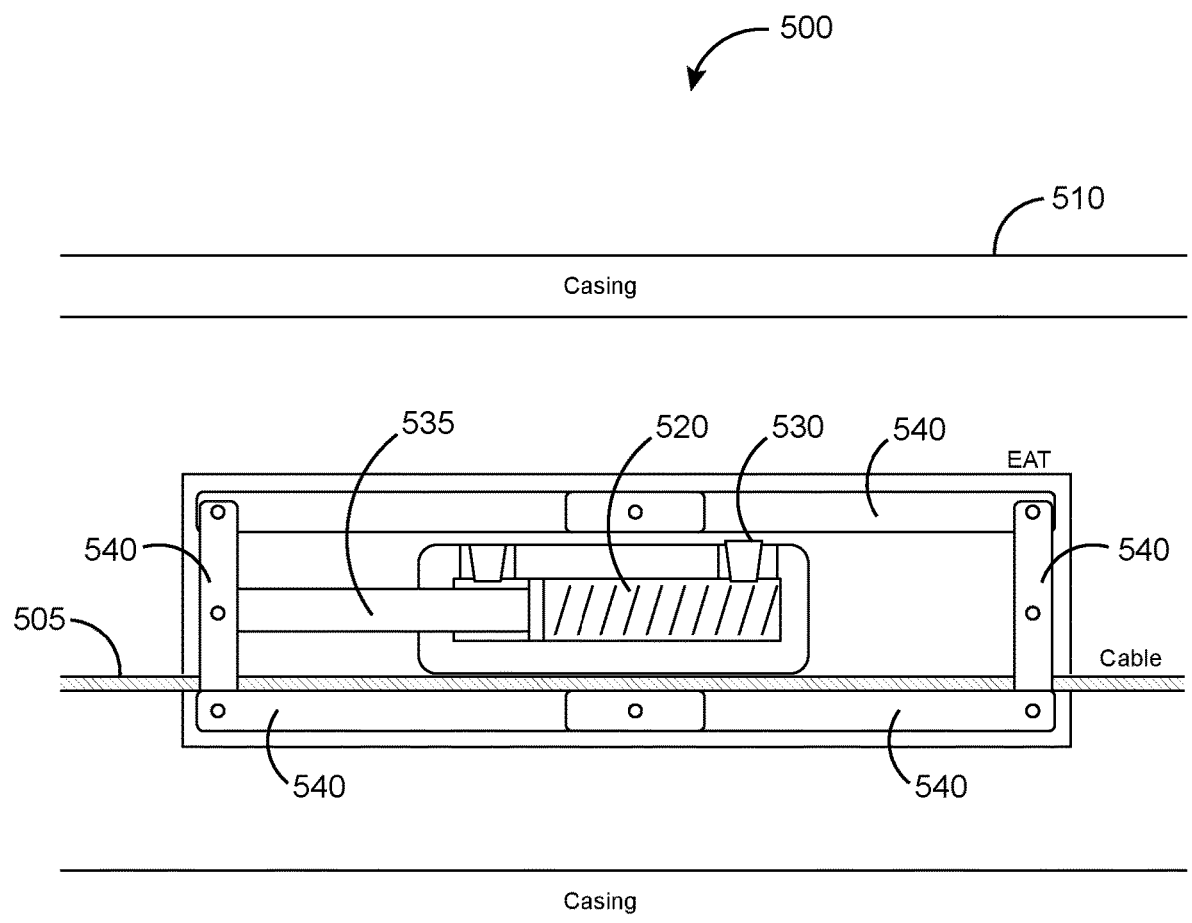
FIG. 5 illustrates EAT now decoupled from wellbore casing and EAT clamped to cable for removal.

Finally, when it is desired to retrieve the EAT module FIG. 5, shown generally as 500, illustrates the result. The casing pressure is increased further to the point that the higher pressure burst disk 530 is triggered to burst. When it bursts, the pressure equilibrates on both sides of the sealed end of the rod 535 and the spring 520 pushes the rod back to its original position, collapsing the arm coupling structure 540 back to its original position and clamping the EAT back on to cable 505. The EAT can then be removed using the wireline/slickline cable 505.

In other embodiments of this proposal the system of translatable EAT modules for deployment along a wellbore casing can be initially attached serially to the downhole tractor and can be individually decoupled from the tractor based on a signal communicated to the tractor that engages a decoupling mechanism and can optionally engage a coupling mechanism to secure the EAT module to the wellbore casing.

Figure 6:
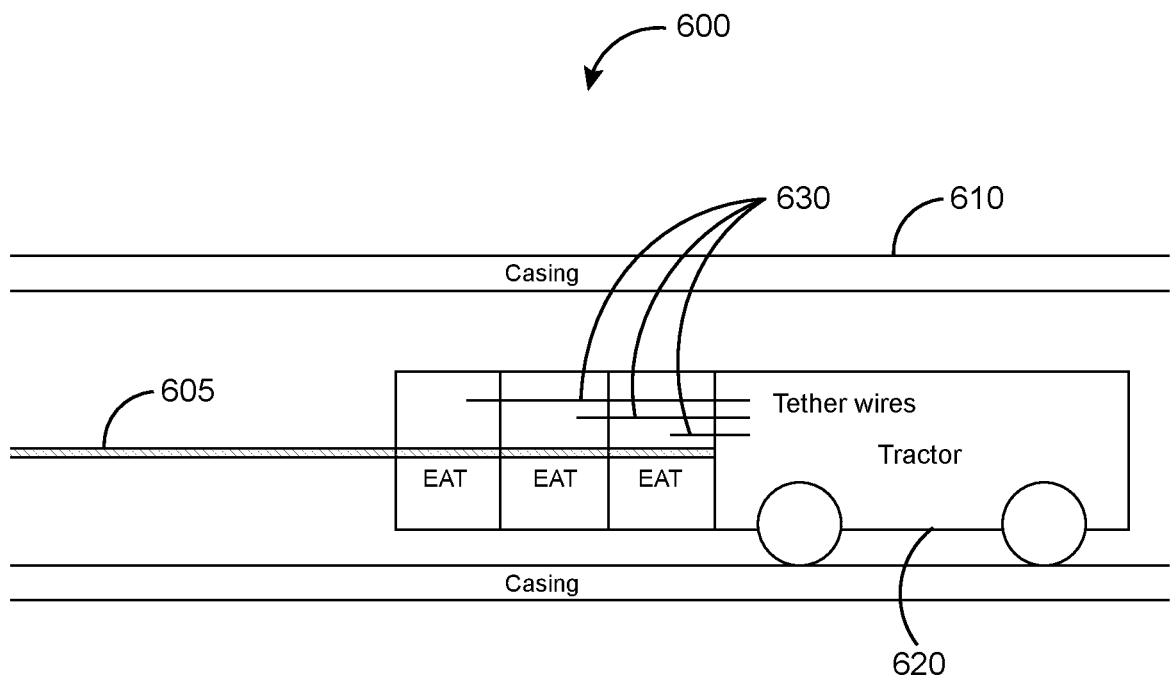
FIG. 6 illustrates a tractor that cuts tether wires individually to release EAT at desired locations.

Referencing FIG. 6, shown generally as 600, a tractor 620 within casing 610 is attached to the end of cable 605 and has three EAT modules attached and secured by tether wires 630. When the tractor has arrived at a desired position, a signal from the surface can be conveyed via the cable to initiate a mechanism to cut the tether wire to the leftmost EAT module. The same or another signal can then initiate another mechanism (to be shown) to couple the EAT module to the wellbore casing 610 at that location.

Figure 7:
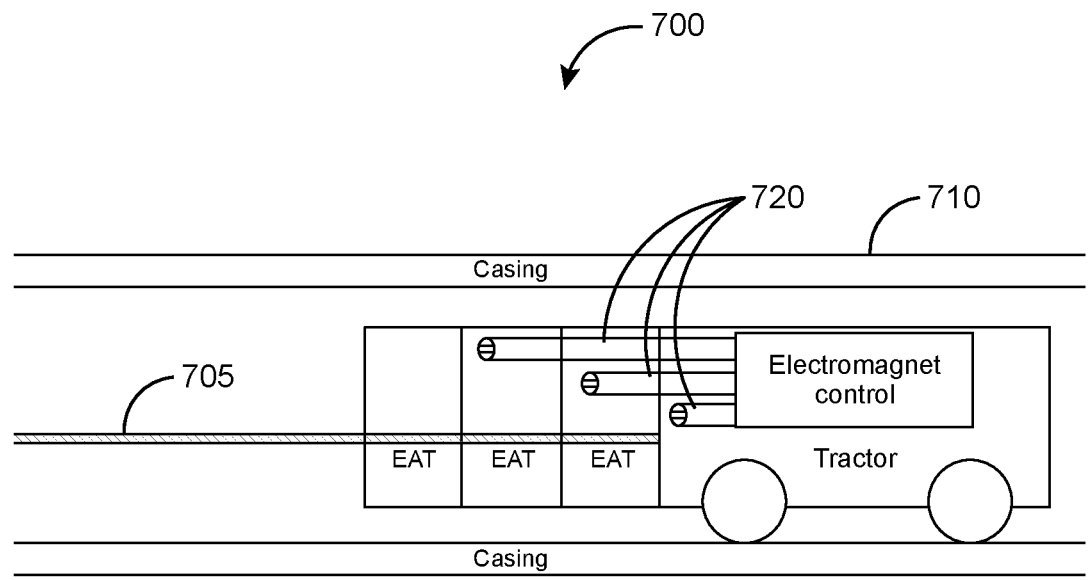
FIG. 7 illustrates a tractor that controls electromagnets to release EAT sensing modules at desired locations.

Similarly, in another approach, FIG. 7 illustrates a tractor within casing 710 attached to the end of a wireline/slickline cable 705 in which three EAT modules are secured to the tractor via electromagnetic rods 720. When the tractor has arrived at a desired position, a signal from the surface can be conveyed via the cable to initiate a mechanism to release the magnetic coupling to each of the EAT modules as they reach their desired positions. The same or another signal can then initiate another mechanism (to be shown) to couple the EAT module to the casing 710 at that location.

Figure 8:
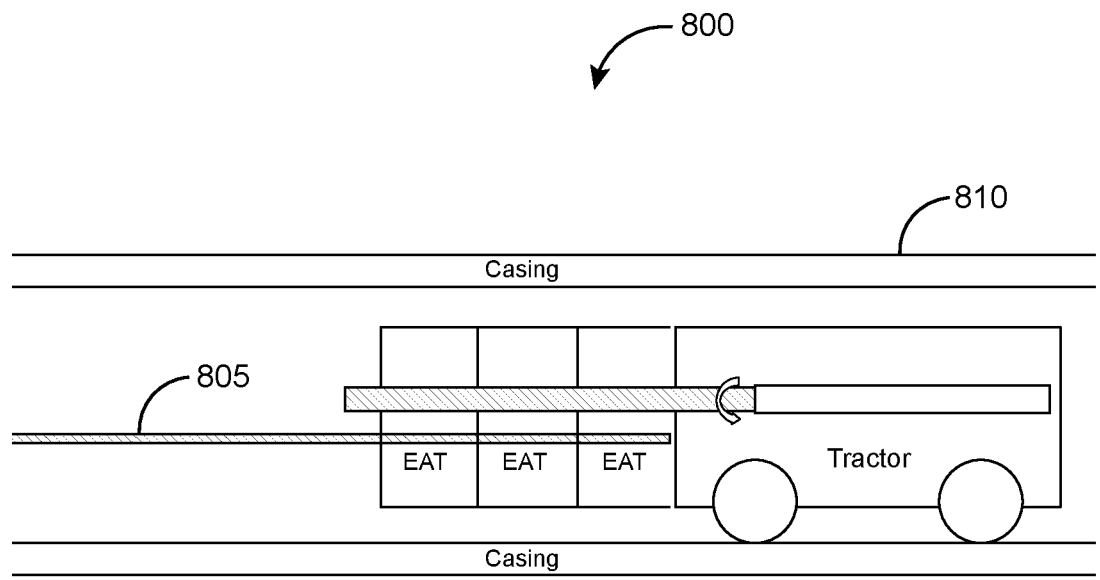
FIG. 8 illustrates a Tractor turns screw to release EAT sensing modules at desired locations.

In another approach, FIG. 8 illustrates a tractor within casing 810 attached to the end of a wireline/slickline cable 805 in which three EAT modules are secured to the tractor via a threaded rod 820. When the tractor has arrived at a desired position, a signal from the surface can be conveyed via cable 805 to initiate a mechanism to retract the threaded rod 820 from each of the EAT modules as they reach their desired positions. The same or another signal can then initiate another mechanism (to be shown) to couple the EAT module to the wellbore casing 810 at that location.

Figure 9:
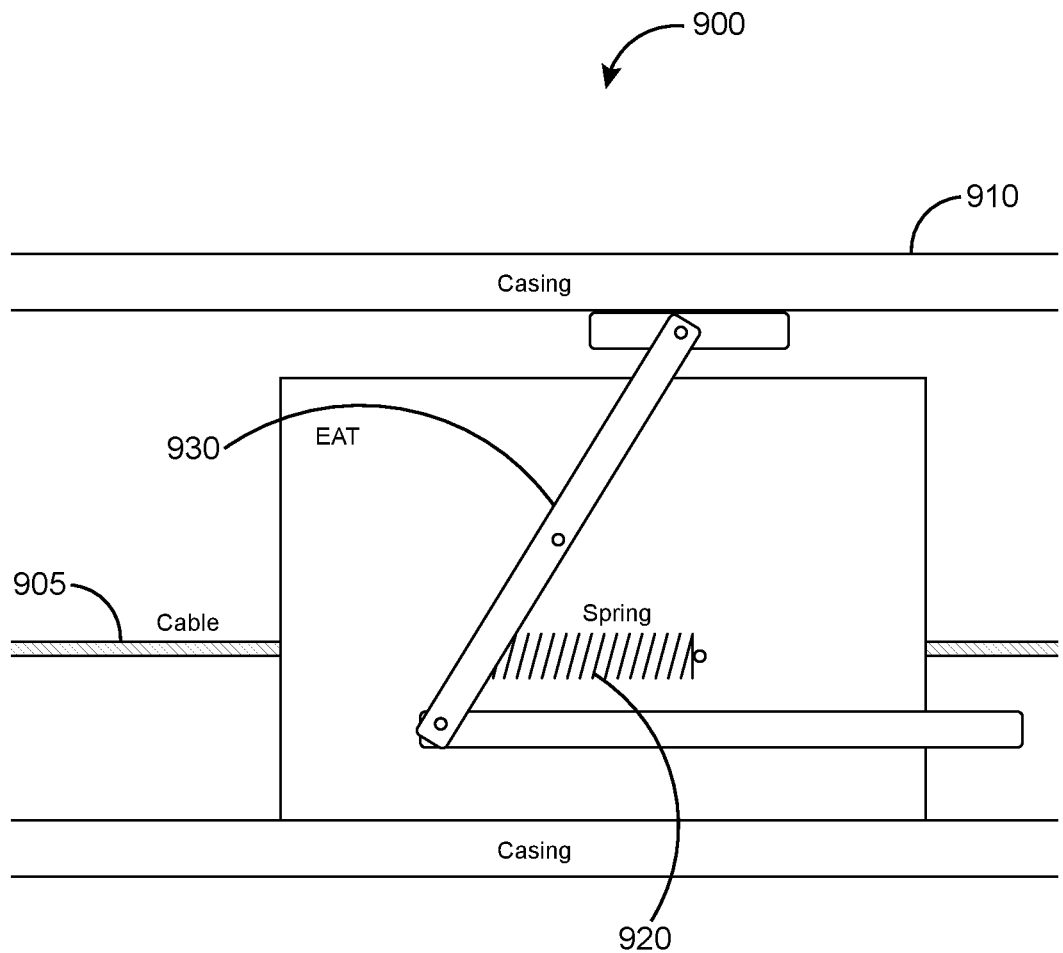
FIG. 9 illustrates an EAT decoupled from a tractor allowing a clamp to deploy to couple the EAT to wellbore casing.

The mechanism to couple each of the EAT modules illustrated in FIGS. 6, 7, and 8 to the well casing is illustrated in FIG. 9, shown generally as 900. A signal conveyed by wireline/slickline cable 905 initiates an internal mechanism that compresses spring 920 to extend arm 930 upward and lock the EAT module against casing 910. The EAT module is not physically connected to cable 905 so the cable can continue to move after the EAT modules are coupled to the wellbore casing.

Figure 10:
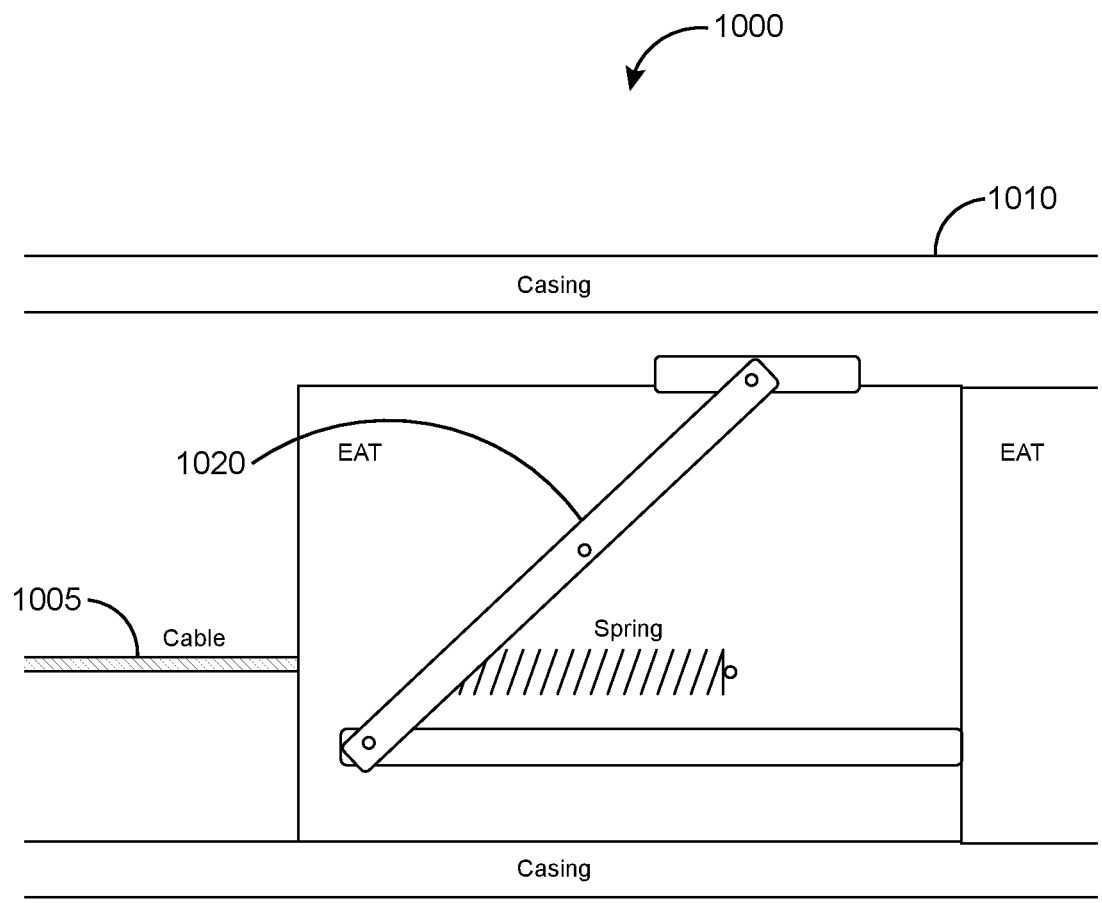
FIG. 10 illustrates how an EAT is decoupled from casing by retraction of clamp lever and then retrieved by an EAT or tractor below it.

As shown in FIG. 10, shown generally as 1000, retrieval of the EAT modules can later be initiated by a signal conveyed by wireline/slickline cable 1005 that decompresses the compressed spring, thereby moving arm 1020 downward and releasing the coupling of the EAT module to the wellbore casing 1010. Retrieval of each of the EAT modules is then accomplished by pulling the cable and tractor back to the surface and collecting each EAT module as it is retrieved.

As each EAT module is located and coupled in desired positions downhole they are used to detect seismic and/or acoustic energy and/or deformations via a distributed acoustic sensing (DAS) interrogator system (not shown) at the surface.

In another embodiment of translatable EAT modules and associated measurement systems an EAT module can optionally be dropped downhole alongside a wireline or slickline optical cable with the EAT module conducting measurements and communicating results via the fiber to a surface interrogator as it moves downhole. These measurements can include pressure and temperature. Both the location and the speed of the EAT module can be tracked via DAS telemetry back to the surface interrogator.

And DTS and/or DAS measurements can be taken simultaneously using the optical fibers in the wireline/slickline fiber optic cable. The DTA and/or DAS measurements would be used with the EAT module data to derive the different fluid flow results described herein.

In a related embodiment multiple EAT modules can be dropped downhole with predetermined intervals. The EAT modules are in close proximity to a wireline/slickline cable but not hard coupled to the cable except for the first/deepest module. As they drop pressure/temperature measurements from at least two modules can be used to derive fluid density.

In another related embodiment using dropped EAT modules acoustic information generated by the modules can be used to measure sound speed and thereby derive oil/water ratio. This technique is described in SPE 77655 (Society of Petroleum Engineers) (2002).

In another related embodiment using dropped EAT modules multi-phase fluid flow information can be derived from the measured data and knowledge of the EAT modules mechanical properties.

In all of these applications using multiple EAT modules dropped downhole retrieval can be done by extraction as a group by extracting of the wireline/slickline cable, since it is coupled to the first/deepest EAT module.

In an alternate embodiment a number of EAT modules designed to be neutrally buoyant or buoyant can be lowered as a group downhole with only the first/deepest EAT module hard connected to the cable. These EAT modules can be individually released and can travel with fluid flow uphole. As they move the EAT modules conduct measurements, including at least temperature and pressure, and communicate the results via the fiber to a surface interrogator. Both the location and speed of the EAT modules can be tracked via DAS telemetry to the surface. Multiple EAT modules can be released with predetermined intervals and at least two modules can be used to derive fluid density. In addition acoustic information generated by the EAT module(s) can be used measure sound speed and thereby derive oil/water ratio (see SPE77655). In addition multi-phase fluid flow information can be derived from the measured data and knowledge of the EAT modules mechanical properties.

In any of the EAT modules described the module can be a sealed unit for high pressure operation.

Value Added

Current logging tools require movement of the entire cable in order to conduct measurements along a wellbore and do not have a method allowing repositioning of tools along cable while downhole.

In releasing tools downhole from cable and retrieving later with cable, the tool weight decreases and load on the tractor decreases the further into the well; Allows for a smaller diameter cable which enables this type of service in high pressure wells.

This approach allows an arrangement that drops the tool along the length of the cable where the tool records on the way down and logs the entire well.

It enables new measurement configurations, and easier and more flexible deployment that can be tailored to well, real time. It also lowers maintenance costs compared to hard wired tools on cables.

Although certain embodiments and their advantages have been described herein in detail, it should be understood that various changes, substitutions and alterations could be made without departing from the coverage as defined by the appended claims. Moreover, the potential applications of the disclosed techniques is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized. Accordingly, the appended claims are intended to include within their scope such processes, machines, manufactures, means, methods or steps.

The invention claimed is:

1. A system of translatable electro acoustic technology (EAT) modules for deployment along an oil or gas wellbore casing comprising:
   a. a wireline/slickline optical distributed acoustic sensing (DAS) cable deployed from a ground surface into the casing and connected to a surface interrogator;
   b. a tractor attached to the downhole end of the wireline/slickline optical distributed acoustic sensing (DAS) cable;
   c. one or more EAT sensing modules configured to be coupled to or decoupled from the wireline/slickline optical distributed acoustic sensing (DAS) cable at pre-selected locations and configured to either be coupled to or decoupled from the casing of the wellbore or be allowed to reposition along the wellbore casing; and
   d. wherein the one or more EAT sensing modules conduct multiple measurements and communicate the results via the wireline/slickline optical distributed acoustic sensing (DAS) cable to a surface interrogator system.

2. The system of translatable electro acoustic technology (EAT) modules for deployment along an oil or gas wellbore casing of claim 1 wherein one or more of the EAT sensing modules are configured to be passed into the wellbore casing as a unit and then distributed along the wellbore casing at selected locations by a coupling/decoupling mechanism.

3. The system of translatable electro acoustic technology (EAT) modules for deployment along an oil or gas wellbore casing of claim 1 wherein the decoupling occurs at a pre-determined pressure by a pressure activated/de-activated plunger connected to coupling arms.

4. The system of translatable electro acoustic technology (EAT) modules for deployment along an oil or gas wellbore casing of claim 1 wherein the one or more EAT sensing modules are configured to be released by a pressure-activated plunger mechanism and the plunger mechanism also moves arms to couple the EAT sensing modules to the casing.

5. The system of translatable electro acoustic technology (EAT) modules for deployment along an oil or gas wellbore casing of claim 1 wherein the use of a tractor attached to the downhole end of the wireline/slickline optical distributed acoustic sensing (DAS) cable is optional, and wherein the one or more EAT sensing modules are not directly coupled to the optical distributed acoustic sensing (DAS) cable and are dropped down the casing at predetermined intervals and conduct one or more measurements as they travel along the wireline/slickline optical distributed acoustic sensing (DAS) cable and communicate the results via DAS telemetry to a surface interrogator system as they move downhole.

6. The system of translatable electro acoustic technology (EAT) modules for deployment along an oil or gas wellbore casing of claim 1 wherein the one or more EAT sensing modules are neutrally buoyant or buoyant EAT sensing modules connected together as a group; and wherein each of the one or more neutrally buoyant or buoyant EAT sensing modules are configured to be released in a predetermined manner to travel with fluid flow uphole.

7. The system of translatable electro acoustic technology (EAT) modules for deployment along an oil or gas wellbore casing of claim 1 wherein the one or more EAT sensing modules are initially attached serially to the tractor and are configured to be individually decoupled upon a signal communicated from the wireline/slickline optical cable to the tractor that engages a decoupling mechanism.

8. The system of translatable electro acoustic technology (EAT) modules for deployment along an oil or gas wellbore casing of claim 7 wherein the signal communicated to the tractor also engages a mechanism to couple the EAT sensing module to the casing of the wellbore by compressing a spring to move a coupling arm against the wellbore casing.

9. The system of translatable electro acoustic technology (EAT) modules for deployment along an oil or gas wellbore casing of claim 8 wherein retrieval of each of the EAT modules is initiated by a signal communicated from the wireline/slickline optical cable that retracts the arm to uncouple the EAT module from the wellbore casing.

10. A method for deploying translatable electro acoustic technology (EAT) modules along an oil or gas wellbore casing comprising:
   a. providing a wireline/slickline optical distributed acoustic sensing (DAS) cable deployed from a ground surface into the casing and connected to a surface interrogator;
   b. providing a tractor attached to the downhole end of the wireline/slickline optical distributed acoustic sensing (DAS) cable;
   c. providing one or more EAT sensing modules configured to be coupled to or decoupled from the wireline/slickline optical distributed acoustic sensing (DAS) cable and configured to either be coupled to or decoupled from the casing of the wellbore or be allowed to reposition along the wellbore; and
   d. wherein the one or more EAT sensing modules conduct multiple measurements and communicate the results via the wireline/slickline optical distributed acoustic sensing (DAS) cable to a surface interrogator system.

11. The method for deploying translatable electro acoustic technology (EAT) modules along an oil or gas wellbore casing of claim 10 wherein one or more of the EAT sensing modules is passed into the wellbore casing as a unit and then distributed along the wellbore casing at selected locations by a coupling/decoupling mechanism.

12. The method for deploying translatable electro acoustic technology (EAT) modules along an oil or gas wellbore casing of claim 10 wherein the decoupling of the one or more EAT sensing EAT modules occurs at a pre-determined pressure by a pressure activated/de-activated plunger connected to coupling arms.

13. The method for deploying translatable electro acoustic technology (EAT) modules along an oil or gas wellbore casing of claim 10 wherein the one or more EAT sensing modules configured to be decoupled by a pressure-activated plunger mechanism and the plunger mechanism also moves arms to couple the EAT sensing modules to the wellbore casing.

14. The method for deploying translatable electro acoustic technology (EAT) modules along an oil or gas wellbore casing of claim 10 wherein the one or more EAT sensing modules are neutrally buoyant or buoyant EAT sensing modules connected together as a group; and wherein each of the one or more neutrally buoyant or buoyant EAT sensing modules are released in a predetermined manner to travel with fluid flow uphole; and conduct measurements as they travel along the wireline/slickline optical distributed acoustic sensing (DAS) cable and communicate the results via the DAS to a surface interrogator system as they move uphole.

15. The method for deploying translatable electro acoustic technology (EAT) modules along an oil or gas wellbore casing of claim 10, wherein the use of the tractor attached to the downhole end of the wireline/slickline optical distributed acoustic sensing (DAS) cable is optional, and the one or more EAT sensing modules are not directly coupled to the optical distributed acoustic sensing (DAS) cable as they are dropped down the oil or gas wellbore casing at predetermined intervals and conduct one or more measurements as they travel along the wireline/slickline optical distributed acoustic sensing (DAS) cable and communicate the results via DAS telemetry to a surface interrogator system as they move downhole.

16. The method for deploying translatable electro acoustic technology (EAT) modules along an oil or gas wellbore casing of claim 15 wherein the EAT sensing modules measure temperatures and pressures that are communicated to the surface via the DAS fiber and used to derive fluid density.

17. The method for deploying translatable electro acoustic technology (EAT) modules along an oil or gas wellbore casing of claim 15 wherein the dropped EAT sensing modules gather acoustic information that can bois used to measure sound speed and thereby derive oil/water ratio.

18. The method for deploying translatable electro acoustic technology (EAT) modules along an oil or gas wellbore casing of claim 10 wherein the one or more EAT sensing modules are initially attached serially to the tractor and configured to be individually decoupled upon a signal communicated from the wireline/slickline optical cable to the tractor that engages a decoupling mechanism.

19. The method for deploying translatable electro acoustic technology (EAT) modules along an oil or gas wellbore casing of claim 18 wherein the signal communicated to the tractor also engages a mechanism to couple the EAT sensing module to the casing of the wellbore by compressing a spring to move a coupling arm against the wellbore casing.

20. The method for deploying translatable electro acoustic technology (EAT) modules along an oil or gas wellbore casing of claim 19 wherein retrieval of each of the EAT modules is initiated by a signal communicated from the wireline/slickline optical cable that retracts the arm to uncouple the EAT module from the wellbore casing.

\* \* \* \* \*

UNITED STATES PATENT AND TRADEMARK OFFICE
CERTIFICATE OF CORRECTION

PATENT NO. : 11,054,536 B2
APPLICATION NO. : 16/338945
DATED : July 6, 2021
INVENTOR(S) : Mikko Jaaskelainen et al.

Page 1 of 1

It is certified that error appears in the above-identified patent and that said Letters Patent is hereby corrected as shown below:

In the Claims

Column 8, Line 63, the portion reading -that can bois used- should read --that is used--

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*